United States Patent [19]

Bayley et al.

[11] Patent Number: 5,043,175

[45] Date of Patent: Aug. 27, 1991

[54] METHOD AND APPARATUS FOR STERILIZATION OF ANIMAL FEED

[75] Inventors: Peter T. Bayley, Duncote; Derek H. Shrimpton, Little Eversden, both of England

[73] Assignee: California Pellet Mill Company, San Francisco, Calif.

[21] Appl. No.: 590,681

[22] Filed: Oct. 1, 1990

[51] Int. Cl.⁵ ............................. A23L 3/00; A61L 2/00
[52] U.S. Cl. ..................................... 426/318; 99/516; 366/147; 422/27; 422/292; 426/511; 426/516; 426/521
[58] Field of Search ............... 426/318, 320, 335, 532, 426/521, 511, 285, 516; 422/27, 292, 305, 307; 99/467, 516; 100/92; 366/147

[56] References Cited

U.S. PATENT DOCUMENTS

| | | | |
|---|---|---|---|
| 3,911,147 | 10/1975 | Barhan et al. | 426/318 |
| 4,001,452 | 1/1977 | Williams | 426/516 |
| 4,021,585 | 5/1977 | Svoboda et al. | 426/332 |
| 4,062,982 | 12/1977 | McMillan et al. | 426/335 |
| 4,145,447 | 3/1979 | Fisher et al. | 426/516 |
| 4,244,978 | 1/1981 | Barta | 426/335 |
| 4,362,753 | 12/1982 | Barta | 426/335 |
| 4,806,353 | 2/1989 | Thomas | 424/141 |

Primary Examiner—George Yeung
Attorney, Agent, or Firm—Walter C. Vliet

[57] ABSTRACT

A method and apparatus for the sterilization of animal feed, wherein a bactericidal agent is mixed with steam for contacting and conditioning animal feed prior to a compaction process as, for instance, a pelletizing process. In one embodiment, chlorine gas is introduced in the burner of a direct fired steam generator to produce a mixture of steam, chlorine, and products of combustion which are introduced to a feed mixture in a blending unit prior to pelletizing, resulting in sterilization of the animal feed.

12 Claims, 2 Drawing Sheets

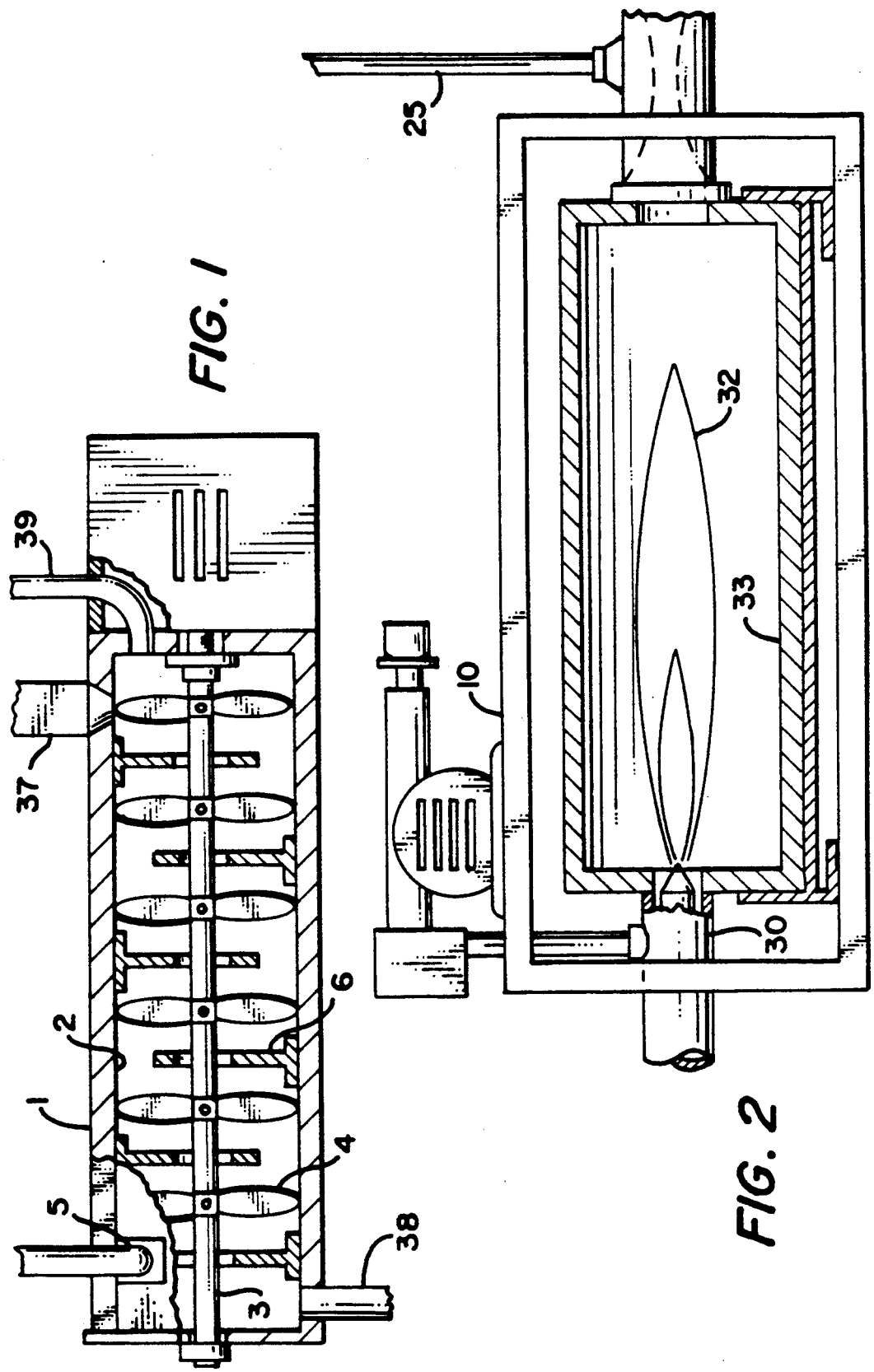

METHOD AND APPARATUS FOR STERILIZATION OF ANIMAL FEED

BACKGROUND OF THE INVENTION

This invention relates generally to apparatus and methods for preparation of animal feed, and more particularly to the preparation of animal feed by pelletizing, including conditioning of the feed before pelletizing.

The presence in food of pathological bacteria is a matter of serious concern. Meat and farm products are particularly at risk, especially poultry and eggs. At each stage in the food chain every attempt has been made to kill bacteria and prevent reinfection. Salmonella are probably the best known pathological bacteria associated with food but other bacteria such as E.coli can occur and produce food poisoning to different degrees of severity.

An important link in the food chain is the manufacture of animal feeds, and it is essential that manufactured animal feed be free from harmful bacteria. Currently, there are a number of methods of killing bacteria in animal feeds with varying degrees of success. Some methods have the disadvantage of destruction of vitamins, others have the disadvantage of high power requirements and high capital costs. Most methods of bacterial kill involve heat and moisture, and provided the correct temperature and retention times are used, the bacterial reduction or kill is effected. Most of the systems involving heat and moisture are situated in the process immediately before the pelleting process and replace the conventional meal conditioning systems.

Typically, the steam used for conditioning and sterilizing is produced from a steam boiler or a vapor generator. Such machines are common and are applied in many industries. To a greater or lesser degree, the systems effect the condition of salmonella in the processed feed. This is accomplished by the combination of temperature and reduced oxygen available to the salmonella or other bacteria. Some bacteria cannot survive in a truly anaerobic atmosphere but salmonella, for instance, can withstand anaerobic conditions, although under such conditions they will not reproduce and in numbers may be reduced. Due to the fact that there is an oxygen component in the water, which is introduced in the products of combustion and there is oxygen in the feed stuff itself, it is difficult to obtain a truly anaerobic conditioning.

The foregoing illustrates limitations known to exist in present devices and methods. Thus, it would be apparent that it would be advantageous to provide an alternative directed to overcoming one or more of the limitations set forth above. Accordingly, a suitable alternative is provided including features more fully disclosed hereinafter.

SUMMARY OF THE INVENTION

In one aspect of the present invention, this is accomplished by providing for the pretreatment of feed products which are to be compressed into a feed product comprising producing a mixture of steam and bactericidal; contacting said mixture with a feed; and subsequently compressing the feed into a feed product.

The foregoing and other aspects will become apparent from the following detailed description of the invention when considered in conjunction with the accompanying drawings.

BRIEF DESCRIPTION OF THE DRAWINGS

FIG. 1 is a schematic cross sectional view of a feed conditioning unit illustrating an embodiment of the feed contacting apparatus;

FIG. 2 is a schematic cross section of a burner and gas producing apparatus according to the present invention;

DETAILED DESCRIPTION

Figure 3:
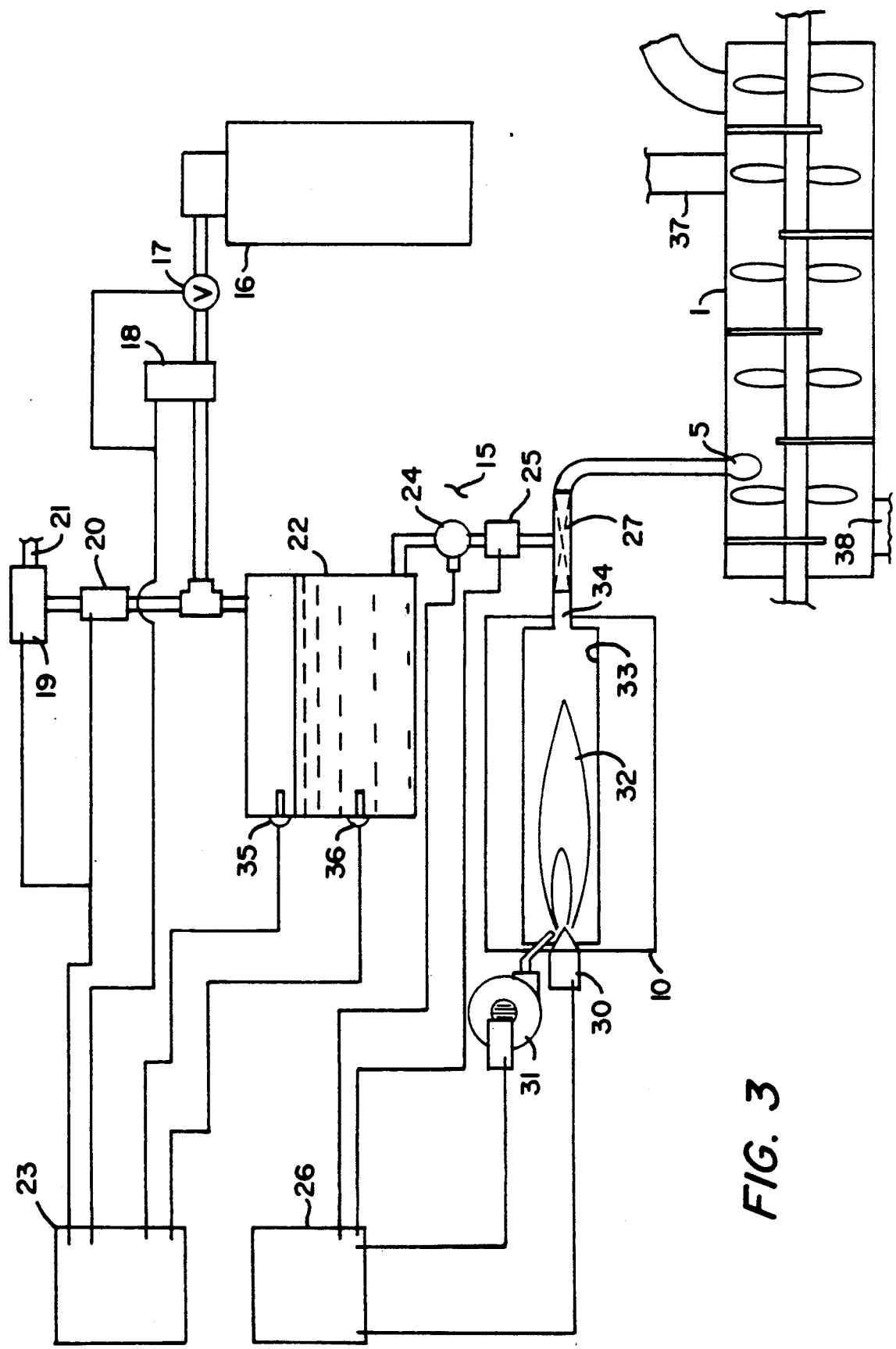
FIG. 3 is a diagrammatic schematic of the apparatus for the pretreatment of feed products which are to be pelletized or otherwise compacted for the treatment of animal feeds in meal form according to the present invention.

In a typical feed conditioning process, prior to pelletizing, steam is contacted with the feed to both moisturize the feed to facilitate its further processing and to effect a degree of bacteria kill.

FIG. 1 shows a contacting vessel 1 for the enhanced contacting of steam products of combustion and a bactericidal agent according to the present invention. The equipment comprises a tubular mixing chamber 2 whose length is determined by the capacity of the system and the retention time required. Concentric within the center of the tubular chamber is a rotating shaft 3 equipped with agitators 4 that both propel material forward through the mixing chamber, and simultaneously effect a thorough mixing of the animal feed passing through the machine. Steam entering inlet 5 is passed through the chamber in a counterflow direction to the feed itself. The mixing chamber may also be fitted with devices, such as baffles, for slowing the passage of the material through the mixing chamber to increase retention and ensure thorough mixing.

FIG. 3 shows a system according to the present invention, wherein steam is produced in a direct fired vapor generator 10 which delivers steam along with the products of combustion to the mixer conditioner unit through inlet 5 previously described. Also depicted in FIG. 3 is a means 15 for delivering chlorinated water to the vapor generator outlet, wherein the chlorinated water mixture is vaporized for delivery to mixer conditioner. The chlorinated water is derived from mixing a chlorine supply 16 with water by means of a control valve 17 and meter 18 which delivers chlorine and a control valve 19 and meter 20 for the water supply 21 delivered to the chlorinated water makeup tank 22, the process being controlled by an electronic chlorine water control device 23 well known in the industries.

Control of the chlorinated water supply to the outlet of the gas generator, is accomplished by means of a chlorinated water control valve 24 and a chlorinated water meter 25 operating through the gas burner control system 26 to coordinate the amount of flow to the burner firing rate. The chlorinated water is educted into the output heated gas and steam stream of the vapor generator, and is educted into that stream by a venturi 27, wherein the temperature of the output of the vapor generator vaporizes the chlorinated water producing a mixture of chlorine, gas, steam, and products of combustion which are then intimately contacted with the feed product in the mixer conditioner 1.

FIG. 3 shows a burner 30 in a vapor generator of the direct fired type contemplated for use in the present invention. A blower 31 furnishes pressurized air to the burner chamber; fuel in the form of liquid or gaseous fuel is introduced in a burner and ignited to form a flame. The flame 32 is produced in a refractory lined combustion chamber 33 and the products of combustion are delivered at the outlet of the combustion chamber 34 under pressure. The products of combustion are passed through a venturi 27, wherein chlorinated water is educted into the products of combustion stream and is vaporized, forming a mixture of products of combustion. The products of combustion, normally carbon dioxide, water vapor, nitrogen, and residual oxygen, will now incorporate the additional moisture vapor or steam formed by the contacting of the products of combustion with the inclement water vapor and the bactericidal agent. The bactericidal agent may be chlorine, sulfur dioxide or liquids, organic acids, such as propionic acid, formic acid, and the like, that are known to kill bacteria by effecting the acidity (PH value) of the animal feed itself.

Although some claims have been made that the resultant mixture of a so-called direct fired steam generator, as described above, is anaerobic, that is, without oxygen, such claims are without foundation. Firstly, there is always a small surplus of oxygen from the combustion process, otherwise dangerous and toxic fumes are produced. Secondly, there is the oxygen component in the water which is introduced into the products combustion. Thirdly, there is oxygen in the feed products itself. Fourthly, although some bacteria cannot survive in a truly anaerobic atmosphere, salmonella can withstand anaerobic conditions, although under such conditions they will not reproduce. Therefore, the mixture of combusted gases and water vapor, not being truly anaerobic, is not totally effective in salmonella kill.

The invention described above, wherein a bactericidal agent is added to the process, improves the potential of the mixture of combusted gases and water vapor to produce total kill and complete sterilization of the animal feed. It is known that very low concentrations of chlorine can be effective in killing bacteria as they have no tolerance to the presence of chlorine. The amount of chlorine to be added to the gases will be variable to permit adjustment of the equipment to allow the lowest level of chlorine to be used for the most effective kill. At the proposed levels of addition, the risk obtained of odor being imparted to the animal feed is negligible.

Under normal operation, the water flow rate into the venturi is quite low due to the low levels of chlorine required for the system. Adding the chlorine to the water immediately before the venturi is not practical, therefore, an arrangement of makeup tank 22 with high and low level controls 35, 36 respectively, as shown, is employed. When the water level falls below the top level, the tank is refilled at full main flow rates up to the high level detection and on reaching this level, the water valve and the chlorine valve is closed. In this way the intermittent, but high flow rate, permits accurate metering and incorporation of the chlorine gas into the liquid. An accurate water meter 19 is provided in the main water supply 21 and a similarly accurate meter 18 is provided with the chlorine supply.

The control valve in the chlorine line is operated by a feedback loop from the chlorine meter and water meter to give accurate and preset rates of addition of chlorine gas in the correct ratio to the incoming water supply. The chlorine gas is dispersed into the water tank by means of a gas/water mixing system (not shown) and held in solution in the water prior to injection into the gas generator system. The water and chlorine in solution are metered from the tank 22 at a rate appropriate to the throughput of the animal feed conditioning and mixing system and the products of combustion from the gas generator.

The steam produced by the system depicted in FIG. 3 will carry the chlorine into the mixing chamber. By virtue of the design of the mixer with its vigorous agitation of the animal feed within the mixing chamber, and the counterflow arrangement of gases through the mixing chamber, the water vapor with chlorine will penetrate between each particle of animal feed to create a micro-climate of combustion gases and water vapor with chlorine in suspension which will condense onto the surfaces of the particular particles, thus producing a chlorine environment to kill the bacteria.

The design of the mixing chamber and the counterflow of gaseous products ensure very rapid transfer of the chlorine from the gas vapor mixture to the animal feed ensuring thorough mixing. As shown in FIGS. 1 and 3, feed enters the mixing chamber 2 at feed inlet 37 and is discharged through feed outlet 38 for further processing or storage. On condensed combustion, gases exit the chamber 2 via vent 39. In such systems that do not use the gas for liquid chlorine additives, such rapid take-up of heat and moisture can be a disadvantage in that the products passing through the mixing chamber are not held at high temperature for sufficient length of time for efficient kill to take place.

Alternatives to the methods of chlorine generation may be used. For example, the makeup tank of FIG. 3 can be accurately metered with additions of sodium hypochlorite which, when metered with the water into the gas stream from the generator, will produce chlorine in the gas stream. In like manner, organic acids can be injected into the system and carried forward through the conditioning system for homogeneous mixing with the animal feed.

It should be understood by one skilled in the art that the invention herein described may be modified in many ways. In addition to the alternatives discussed above, it should be obvious that mixing may be accomplished in vertical agitated vessels and that the steam may be produced in other conventional ways which will now be apparent to those skilled in the art.

Having described the invention, what is claimed is:

1. A method for the pretreatment of feed products which are compacted, comprising the steps of:
   producing a mixture of steam and a vaporized bactericidal;
   contacting said mixture with a feed to form a uniform intimate feed mixture of steam, bactericidal, and feed; and
   subsequently delivering and forming said feed mixture into a compacted feed product.

2. A method according to claim 1, wherein said mixture comprises direct fired steam plus a bactericidal gas such as chlorine formed from water containing said bactericidal which is vaporized by said direct fired steam.

3. A method according to claim 1, wherein said mixture comprises a direct fired steam plus an organic acid.

4. A method according to claim 2, wherein said mixture is contacted in a counterflow heat exchanger.

5. A method for the treatment of feed products according to claim 1, wherein said mixture is an animal feed product.

6. A method according to claim 1, wherein said forming of the feed product is accomplished in a pellet mill.

7. A method according to claim 1, wherein said forming of the feed product is accomplished in a roll mill.

8. A method according to claim 1, wherein said forming of the feed product is accomplished in an extruder.

9. A method according to claim 1, wherein said mixture and said feed are agitated during conditioning.

10. An apparatus for the pretreatment of feed products which are to be compressed into a feed product, comprising:
    means for producing a mixture of steam and a bactericidal;
    means for contacting said mixture with a feed to form a uniform intimate feed mixture of steam, bactericidal and feed; and
    means for compressing said feed into a feed product.

11. An apparatus for the pretreatment of feed products according to claim 10, wherein said means for producing steam comprises:
    a direct fired steam boiler producing steam and products of combustion;
    means for contacting the steam produced with chlorine and the feed;
    means for mixing the mixture;
    means for compacting the mixture; and
    said means for compacting the mixture comprises a pellet mill.

12. An apparatus for the pretreatment of feed products according to claim 10, wherein said means for producing steam comprises:
    a direct fired steam boiler producing steam and products of combustion;
    means for contacting the steam produced with chlorine and the feed;
    means for mixing the mixture;
    means for compacting the mixture; and
    said means for compacting the mixture comprises a roll mill.

* * * * *